(12) United States Patent
Harvey

(10) Patent No.: US 9,840,676 B1
(45) Date of Patent: Dec. 12, 2017

(54) DIESEL AND TURBINE FUELS FROM ETHANOL

(71) Applicant: The United States of America as Represented by the Secretary of the Navy, Washington, DC (US)

(72) Inventor: Benjamin G. Harvey, Ridgecrest, CA (US)

(73) Assignee: The Goverment of United States of America as Represented by to Secretary of the Navy, Washington, DC (US)

(*) Notice: Subject to any disclaimer, the term of this patent is extended or adjusted under 35 U.S.C. 154(b) by 164 days.

(21) Appl. No.: 15/195,257

(22) Filed: Jun. 28, 2016

Related U.S. Application Data

(63) Continuation-in-part of application No. 13/951,040, filed on Jul. 25, 2013, now abandoned.

(60) Provisional application No. 61/676,203, filed on Jul. 26, 2012.

(51) Int. Cl.
| | |
|---|---|
| *C07C 1/24* | (2006.01) |
| *C07C 2/08* | (2006.01) |
| *C07C 5/03* | (2006.01) |
| *C10L 1/08* | (2006.01) |
| *C10G 50/00* | (2006.01) |
| *C10G 45/00* | (2006.01) |
| *C10L 1/04* | (2006.01) |

(52) U.S. Cl.
CPC ...... *C10L 1/08* (2013.01); *C07C 1/24* (2013.01); *C07C 2/08* (2013.01); *C10G 45/00* (2013.01); *C10G 50/00* (2013.01); *C10L 1/04* (2013.01); *C10G 2300/1088* (2013.01); *C10G 2400/04* (2013.01); *C10L 2200/0469* (2013.01); *C10L 2270/026* (2013.01); *C10L 2270/04* (2013.01); *C10L 2290/08* (2013.01); *C10L 2290/543* (2013.01)

(58) Field of Classification Search
CPC ................ C07C 1/24; C07C 2/08; C07C 5/03
USPC ....... 585/324, 326, 327, 329, 510, 511, 517, 585/639, 640, 275
See application file for complete search history.

(56) References Cited

U.S. PATENT DOCUMENTS

| | | | |
|---|---|---|---|
| 4,434,313 | A | 2/1984 | Langer, Jr. |
| 4,670,620 | A | 6/1987 | Jacobs et al. |
| 5,500,398 | A | 3/1996 | Marks |
| 2002/0035029 | A1 | 3/2002 | Yoshida et al. |
| 2003/0013623 | A1 | 1/2003 | Tse et al. |
| 2009/0036725 | A1 | 2/2009 | Wu et al. |
| 2011/0113679 | A1 | 5/2011 | Cohen et al. |

FOREIGN PATENT DOCUMENTS

| | | |
|---|---|---|
| WO | WO 2009/070858 | 6/2009 |
| WO | WO 2010/066830 | 6/2010 |

OTHER PUBLICATIONS

Cited by Examiner is parent case: Kissin, Detailed Kinetics with 1-Hexene Oligom'n Rxn with (n-Bu-Cp)2ZrCl2-MAO Catalyst, Macrom'r Chem. & Physics (2009), 210, pp. 1241-1246.

Cited by Examiner is parent case: Anslyn ("Modern Physical Organic Chemistry", University Science Books: 2006; p. 796.

Amin N.A.S. and Anggoro D. D.J. Nat Gas Chem 11 :79-86 (200.2).

*Primary Examiner* — Thuan D Dang
(74) *Attorney, Agent, or Firm* — Charlene A. Haley

(57) ABSTRACT

A three step method for the conversion of ethanol into fuels that can be utilized as full-performance military jet or diesel fuels. Embodiments of the invention further describe methods for the selective conversion of ethanol to full performance saturated hydrocarbon fuels that are suitable for both jet and diesel propulsion.

25 Claims, 5 Drawing Sheets

DIESEL AND TURBINE FUELS FROM ETHANOL

CROSS-REFERENCE TO RELATED APPLICATIONS

This is a continuation-in-part patent application, claiming benefit of parent application Ser. No. 13/951,040 filed on Jul. 25, 2013, which is a non-provisional patent application, claiming the benefit of, parent application Ser. No. 61/676,203 filed on Jul. 26, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods for the selective conversion of ethanol to full performance saturated hydrocarbon fuels that are suitable for both jet and diesel propulsion.

Figure 1:
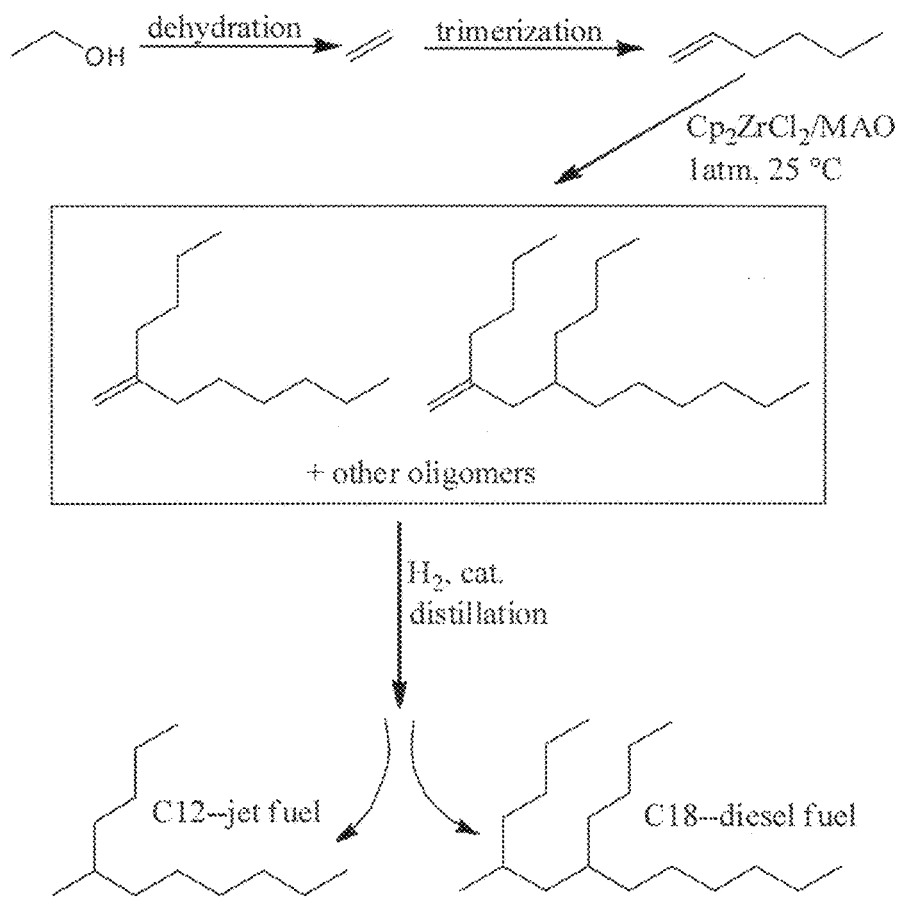
FIG. 1 is a flow chart showing conversion of ethanol to full-performance jet and diesel fuels, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to methods for the selective conversion of ethanol to full performance saturated hydrocarbon fuels that are suitable for both jet and diesel propulsion.

Ethanol is the most widely produced biofuel in the world, with global production estimated at 73 billion gallons per year in 2030. Ethanol is primarily blended with gasoline due to its impressive octane number, but is unsuitable for use in military jet fuel due to its low density and net heat of combustion coupled with its relatively high corrosivity and miscibility with water. Ethanol can be readily dehydrated to the molecule ethylene by reaction with an acidic catalyst at elevated temperature. Oligomerization of ethylene produces linear molecules which have utility as diesel and jet fuels, however conventional approaches produce straight chain molecules that have relatively high melting points and limit the amount of these molecules that can be blended with conventional jet fuels. In contrast, the current approach selectively converts ethylene to 1-hexene which is then oligomerized with a Ziegler Natta catalyst to dimers and trimers, C12 and C18 molecules respectively. Due to the catalyst utilized for the oligomerization, these products have well-defined chain branching which greatly reduces the freezing point of the fuels, but due to the length of the chain, does not adversely affect the cetane number of the fuels. Therefore, fuels produced in this manner are suitable for both jet and diesel propulsion.

The oligomerization of ethylene to produce gasoline range fuel(s) is described in: Amin N. A. S. and Anggoro D. D. J. Nat Gas Chem 11:79-86 (2002). A process for the conversion of bioethanol to polyethylene is described in: Morschbacker A Polym Rev 49:79-84 (2009). A process for the conversion of bioethanolIbiobutanol to low density polyethylene is described in: Morschbacker, A and de Castro, L. R. WIPO Patent WO 20091070858 (2009). 1-hexene dimerization/oligomerization with an unselective heterogeneous catalyst is described in: U.S. Pat. No. 6,737,555.

Embodiments of the invention describe a three step method for the conversion of ethanol into fuels that can be utilized as full-performance military jet or diesel fuels. Embodiments of the invention further describe methods for the selective conversion of ethanol to full performance saturated hydrocarbon fuels that are suitable for both jet and diesel propulsion. These sustainable fuels can be produced domestically from biomass and will help the Navy to meet its goals of reducing petroleum usage while reducing greenhouse gas emissions.

1. Ethanol generated from either a renewable source (i.e. sugars, cellulosic or lignocellulosic feedstocks, $CO_2$, bio-derived syngas) or a petrochemical source is dehydrated by use of a heterogeneous catalyst (e.g. alumina) to produce ethylene.

2. Ethylene is selectively converted to 1-hexene by reaction with an ethylene trimerization catalyst (Ti, Cr, Ta, or Zr-based).

3. 1-hexene is converted to a mixture of dimers and trimers by reaction with a Ziegler Natta catalyst system—this can be accomplished through either a batch or continuous process, either with or without the addition of a chain transfer catalyst.

4. The mixture of oligomers is hydrogenated and distilled to produce a $C_{12}$ and $C_{18}$ distillate, respectively.

5. Pot residue can be further vacuum distilled to produce a synthetic oil.

1. Ethanol from any source can be used in this invention. The ethanol is dehydrated to ethylene in a continuous process utilizing a low acidity alumina catalyst at elevated temperature (250-400 degrees C.) and under an inert atmosphere. Water from the dehydration process is condensed, while ethylene is thoroughly dried by passage through a suitable drying agent (i.e. molecular sieves, calcium sulfate). At this point ethylene can be condensed under increased pressure or utilized in a multi-step, downstream process. Ethanol/water solutions can also be used in the dehydration process, although higher concentrations of ethanol are another embodiment.

2. Ethylene is oligomerized to 1-hexene. When unselective catalysts are used, a fractional distillation is required to isolate pure 1-hexene. In contrast, highly selective chromium and titanium based catalysts can be utilized to produce almost exclusively 1-hexene. This can be conducted by either a batch or continuous process. The presence of heavier oligomers including 1-octene or 1-decene do not negatively impact the overall process. In another embodiment of the invention, an unselective catalyst can be used and separated into a $C_6$-$C_8$ fraction, a $C_{10}$-$C_{14}$ fraction, a $C_{16}$-$C_{20}$ fraction, and a $C_{20}$+ fraction. The $C_6$-$C_8$ fraction can be selectively oligomerized as described below while the $C_{10}$-$C_{14}$ fraction can be directly hydrogenated and incorporated into the jet/diesel fuel formulation. The $C_{16}$-$C_{20}$ fraction can be incorporated in limited amounts in jet fuels or significant amounts in diesel fuel.

3. Pure 1-hexene, or a mixture of 1-hexene/1-octene is oligomerized to produce a product mixture primarily consisting of dimers and trimers. In the case of pure 1-hexene, the products would be 5-methyleneundecane and 7-butyl-5-methyleneundecane. Metallocene based catalysts of the group 4 elements, including Ti, Zr, Hf and other catalysts known in the art to selectively generate 1,2-addition products are suitable for this step. A cocatalyst comprised of an aluminum alkyl or methylaluminoxane is required for catalysis to take place. The cocatalyst can be added to achieve M:Al ratios of from about 1 up to about 500. The Ziegler Natta catalysts can be added in olefin: M ratios of from about 1,000,000:1 to about 5000:1. Higher catalyst loadings result in shorter reaction times. In an embodiment of the invention, a chain transfer agent such as a zinc alkyl compound can be added to alter the distribution of oligomers. The typical zinc alkyl loading for an olefin: M ratio of 100:1 is between 2 and 8 equivalents.

4. The product oligomers are catalytically hydrogenated utilizing nickel, copper, palladium, platinum, or ruthenium catalysts under a hydrogen atmosphere. Temperatures ranging from ambient up to 200 degrees C. and at pressures from 1 atm up to ~50 atm are suitable for this process. After hydrogenation, the product mixture is fractionally distilled to isolate 5-methylundecane and 7-butyl-5-methyltridecane, respectively.

5. The pot residue from the process described in 4 can be vacuum distilled at temperatures up to about 250 degrees C. to capture heavier oligomers with utility as oils and lubricants.

Despite extensive worldwide efforts to generate renewable fuels from biomass, several prominent studies have concluded that conversion of biomass to electricity is the most efficient use of these resources. Through this approach, one would envision fleets of electric vehicles powered by bio-electricity with a transition to solar electricity as capacity, photovoltaic efficiency, and storage capabilities improve. Although the widespread development of bio-electricity is important and expected to play a rote in both transportation and other power requirements, it does not address the long term need for renewable jet and diesel fuels to power aircraft, heavy trucks, and ships.

Although new methods for the production of renewable fuels continue to be developed, none of these fuels have challenged the supremacy of ethanol as the dominant biofuel platform. 22 billion gallons of ethanol were produced in 2011 and this trend is expected to continue with global production of ethanol estimated at 73 billion gallons by 2030. There are a number of reasons for this remarkable projected output. First, the technology required to generate ethanol at impressive titers and with robust microorganisms has been around for thousands of years. Second, the infrastructure required to produce ethanol on a massive scale is already in place along with well established methods for the purification, distribution, and formulation of ethanol with petroleum-based fuels. Third, a considerable amount of effort has been expended to efficiently generate ethanol from cellulosic feedstocks. This emerging technology has the potential to deliver significant quantities of fuel in a sustainable manner and according to a recent DOE study, conversion of waste biomass to renewable fuels can sustainably offset up to 30% of U.S. transportation fuels. To take advantage of the increasing production of bio-ethanol, new approaches for converting it to full-performance jet and diesel fuels need to be developed.

The first step in generating a full-performance (drop-in) renewable fuel is to remove oxygen. In the case of ethanol, this can be readily accomplished by dehydration to ethylene. This process can be conducted with widely available industrial catalysts including γ-alumina, zeolites, and heteropolyacids. Some of the most promising catalysts based on phosphorus/lanthanum modified HZSM-5 give 100% conversion of ethanol with greater than 99% selectivity to ethylene. Compared to other biofuel deoxygenation methods, the generation of a gaseous hydrocarbon greatly simplifies the purification process, while the product can be stored under pressure or transferred via a pipeline. Some dehydration catalysts can be used in the presence of significant quantities of water which allows for ethanol concentration and conversion steps to be combined. Dual purpose catalysts have been developed that both dehydrate ethanol and oligomerize the resulting ethylene to generate gasoline-range hydrocarbon mixtures and even higher molecular weight distillate fuels. Although this combined approach offers a number of advantages including simplified reactor constructs without the need for additional heating/cooling cycles, the product distribution is difficult to control and a significant amount of light hydrocarbons are generated.

In addition to ethylene derived from bio-ethanol, increasing amounts are now being produced in the United States from abundant shale gas. Regardless of the source, synthetic fuels based on ethylene will be well poised to take advantage of this important resource and may offer efficient alternatives to conventional gas-to-liquids (GTL) fuel production processes.

The most straightforward route for conversion of ethylene to jet and diesel fuels relies on direct oligomerization of ethylene. This process, conducted with the aid of heterogeneous catalysts, has been well studied. One of the earliest olefin oligomerization catalysts supported polyphosphoric acid. More recently, studies have focused on ethylene oligomerization with zeolites and acidic mesoporous catalysts. For all of these catalysts the conversion to diesel range hydrocarbons is low. Acidic catalysts oligomerize olefins through carbocation intermediates. Due to the greater stability of tertiary carbocations, these catalysts generate highly branched hydrocarbons. Although these hydrocarbons are excellent for gasoline and some of the heavier branched hydrocarbons are suitable for incorporation in jet fuel, they cannot be used extensively in diesel fuel due to their low cetane numbers. A way to extend the hydrocarbon chain length to improve the cetane number is to incorporate active metals (i.e. nickel) into zeolites, and amorphous or mesoporous catalysts. In the latter case, yields of $C_{10+}$ oligomers have been reported in the range of 23-41% by mass. More recently, a two step process that consisted of conversion of ethylene to a mixture of C4-C10 olefins over nickel-exchanged AlMCM-41, followed by acid-catalyzed reaction over H-MCM-41, was capable of generating jet/diesel range fuels.

To overcome the difficulties in selectively generating jet and diesel range hydrocarbons from ethanol, we became interested in utilizing 1-hexene as a renewable C6 platform for fuel synthesis (FIG. 1). There are a number of reasons why 1-hexene is intriguing as an intermediate to full-performance fuels. First, with a boiling point of 63° C., 1-hexene can be stored and transported in a similar manner to gasoline. Second, 1-hexene is an important industrial chemical used as a co-monomer with ethylene for the generation of linear low-density polyethylene and is produced on a commercial scale. Finally, 1-hexene can be efficiently generated from ethylene with the aid of a variety of homogenous catalysts.

The most prominent examples of homogenous ethylene oligomerisation catalysts are the SHOP (Shell Higher Olefin Process)-type catalysts which generate a broad range of linear oligomers from ethylene. With regard to selective oligomerization methods, the most elegant examples can be found for ethylene trimerization. Chromium catalysts as well as titanium, zirconium, and tantalum based catalysts have been shown capable of converting ethylene to 1-hexene with selectivities up to 99% under moderate conditions. Other relevant work on the development of C6 platforms for renewable fuels has focused on biosynthetic routes to 1-hexanol, while recent reports have described the biosynthesis of caproic acid from dilute ethanol and the conversion of caproic acid to 1-hexanol with carboxydotropic bacteria. Regardless of the source, bio-1-hexanol can be converted to 1-hexene with selectivities above 95% for the normal olefin by dehydration with γ-alumina at 300° C. FIG. 1 shows a conversion of ethanol to full-performance jet and diesel fuels Given the promise of bioderived ethylene and 1-hexene as deoxygenated precursors to full-performance fuels, the current work discusses the oligomerization of 1-hexene to selectively generate both jet and diesel fuels.

EXPERIMENTAL

General Methods

All organometallic manipulations were carried out using standard Schlenk techniques under an atmosphere of purified nitrogen. 1-hexene was stirred over $CaH_2$ and distilled under nitrogen prior to use. MAO (10% in toluene), 10% Pd/C, and $Cp_2ZrCl_2$ were obtained from commercial suppliers and used as received. $^1H$ and $^{13}C$ NMR spectra were collected on a 300 MHz ($^1H$), 75 MHz ($^{13}C$) spectrometer in $CDCl_3$ and referenced to the residual solvent peaks ($^1H$, δ 7.27; $^{13}C$, δ77.16). Mixtures and pure compounds were analyzed with a gas chromatography (GC) system equipped with an RTX-5MS 30-meter column. The GC inlet temperature was 250° C., the initial column temperature was 40° C. held at 3 min, and the temperature was increased at 10° C. min$^{-1}$ up to a final temperature of 350° C. A mass selective detector was used to help identify the sample components. Thermomechanical analysis of fuel samples and viscosity measurements were conducted as described previously. Cetane numbers were determined by ignition quality testing (IQT) conducted at the Southwest Research Institute. Flash-points were measured using ASTM D7094 on a Grabner Instruments Miniflash FLP. Elemental analysis was performed by Atlantic Microlabs, Norcross Ga.

Figure 2:
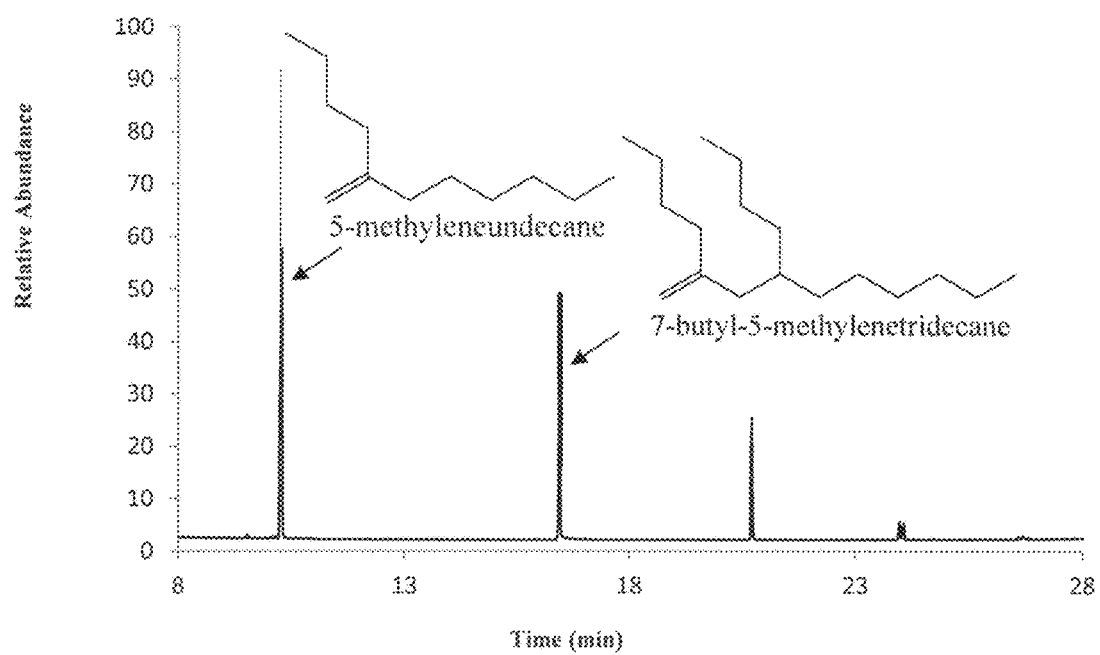
FIG. 2 is a graph illustrating a GC Chromatogram showing the hexene oligomer distribution, according to embodiments of the invention.

Oligomerization of 1-hexene $Cp_2ZrCl_2$ (385 mg, 1.32 mmol) was dissolved in 10% MAO in toluene (44 mL, 66.4 mmol) to yield a pale yellow solution which transitioned to a golden color while being stirred at ambient temperature for 1 h. The solvent was then removed under reduced pressure (1 mm Hg) to give a pyrophoric yellow solid. The solid was broken up into a powder with a spatula under a flow of nitrogen and the flask sealed with a septum. The flask was then cooled in an ice water bath and freshly distilled 1-hexene was slowly added down the side of the flask until ~20 mL had collected. An additional 780 mL of 1-hexene was then added to the slimy via a pressure-equalized addition funnel over the course of two hours. The slurry transitioned to a red solution and the ice bath had to be maintained throughout the course of the addition due to the exothermic reaction. After the addition was complete, the funnel was replaced with a reflux condenser and the flask was allowed to warm to room temperature. The temperature was maintained at 25-30° C. for the duration of the reaction with the aid of a water bath. The reaction was monitored by $^1H$ NMR spectroscopy and after all the 1-hexene was consumed (~16 h), the catalyst was quenched by addition of 3 mL of water. The mixture was filtered through a short plug of alumina to give 525 g (98%) of a colorless liquid that was then analyzed by GC. Although the relative amounts of oligomers differed slightly between batches, a typical distribution was: 56% dimer, 25% trimer, 13% tetramers, 5% pentamers, and 1% hexamers. FIG. 2 is a graph illustrating a GC Chromatogram showing the hexene oligomer distribution.

5-methylencundecane

The oligomer mixture was distilled through an 18" Vigreux column at atmospheric pressure. The fraction distilling from 185-200° C. was collected to yield the compound in >98% purity. $^1H$ NMR (CDCl$_3$) δ: 4.73 (s, 2H, =CH$_2$), 2.04 (t, J=7.2 Hz, 4H, α-CH$_2$), 1.52-1.28 (m, 12H, CH$_2$), 0.98-0.88 (overlapping triplets, 6H, CH$_3$). $^{13}C$ NMR (CDCl$_3$) δ; 150.4 (quat. C=C), 108.7 (=CH$_2$), 36.4, 36.1, 32.2, 30.4, 29.5, 28.1, 23.0, 22.8, 14.3, 14.2. Anal. Calcd for $C_{12}H_{24}$: C, 85.63; H, 14.37. Found: C, 85.76; H, 14.53.

5-methylundecane

10% Pd/C (2 g, 1.88 mmol Pd) was added to 5-methyleneundecane (385 g, 2.29 mol) in a glass bomb. The bomb was evacuated and back-filled with hydrogen several times and the pressure then maintained at 50 psi. The reaction mixture was vigorously shaken until hydrogen uptake ceased. The mixture was then filtered through a pad of celite to give 380 g (98% yield) of the product. $^1H$ NMR (CDCl$_3$) δ: 1.30 (bs, 15H), 1.20-1.05 (m, 2H), 0.98-0.84 (overlapping triplets, 9H, CH$_3$). $^{13}C$ NMR (CDCl$_3$) δ: 37.5, 37.2, 33.1, 32.4, 30.1, 29.7, 27.5, 23.4, 23.1, 20.0, 14.42, 14.38. Anal. Calcd for $C_{12}H_{26}$: C, 84.61; H, 15.39. Found: C, 84.77; H, 15.49.

7-butyl-5-methylenetridecane

The residual oligomer mixture was distilled under reduced pressure (~1 Torr) and the fraction distilling from 95-110° C. was collected to yield the compound in >95% purity. $^1$H NMR (CDCl$_3$) δ: 4.77 (s, 1H), 4.72 (s, 1H), 2.07-1.93 (overlapping triplets, 4H), 1.60-1.20 (m, 21H), 0.99-0.89 (overlapping triplets, 9H, CH$_3$). $^{13}$C NMR (CDCl$_3$) δ: 148.8 (quat. C=C), 110.0 (=CH2), 41.3, 35.4, 35.2, 33.5, 33.2, 32.0, 30.0, 29.8, 28.8, 26.5, 23.1, 22.7, 22.5, 14.1, 14.0, 13.9. Anal. Calcd for C$_{18}$H$_{36}$: C, 85.63; H, 14.37. Found: C, 85.65; H, 14.51.

7-butyl-5-methyltridecane

This compound was prepared from 7-butyl-5-methylenetridecane as described above. $^1$H NMR (CDCl$_3$) δ: 1.6-1.1 (bs, 26H), 1.0-0.8 (m, 12H, CH$_3$). $^{13}$C NMR (CDCl$_3$) δ: 42.42, 42.41, 37.6, 35.1, 34.7, 34.3, 34.0, 33.6, 32.3, 30.5, 30.3, 30.2, 29.6, 29.3, 29.0, 27.0, 26.7, 23.6, 23.5, 23.4, 23.1, 20.3, 14.5, 14.4. Anal. Calcd for C$_{18}$H$_{38}$: C, 84.95; H, 15.05. Found: C, 85.05; H, 15.11.

Some of our previous work in the synthesis of renewable fuels and plasticizers focused on the use of bio-1-butene (ideally derived from n-butanol) as a feedstock to jet and diesel fuels. In that work, primarily trimer and tetramer (C12 and C16), were targeted so that the resulting hydrocarbon mixture would have a suitable flashpoint and density. A Cp$_2$ZrCl$_2$/MAO catalyst with an Al/Zr ratio of 100 was utilized to increase the amount of trimer and tetramer, while reducing the amount of dimer formed. In the case of 1-hexene, the two oligomers of interest are the dimer and trimer (C12 and C18) and this required a change in the distribution of products. A variety of zirconocene-based catalysts have been studied for hexene oligomerization, but as the commercially available Cp$_2$ZrCl$_2$ has been shown to possess suitable activity and the ability to produce specific product distributions, it was used in the current work. To eliminate higher molecular weight oligomers, a low Al/Zr ratio can be used, but at the expense of the TON.

To generate primarily dimer, but sufficient trimer to fully investigate its properties, the catalyst was prepared by addition of 50 equivalents of MAO to Cp$_2$ZrCl$_2$ followed by removal of both the solvent and residual AlMe$_3$ in vacuo. 1-hexene was used as both the solvent and the reactant and shortly after addition of 1-hexene, a clear red solution was formed. Although it was somewhat surprising that the catalyst would have sufficient solubility in the non-polar alkene to give a homogenous solution, it is likely that the catalyst only becomes soluble after coordination/insertion of the olefin. The TON of the catalyst approached 5000 and although higher TONs could be achieved, the ratio of catalyst to olefin was selected so that full conversion of 1-hexene was obtained and the reaction was complete after 16 hours at ambient temperature. Initially the reaction was exothermic and the addition had to be carefully controlled in order to keep the temperature stable. GC analysis of the product mixture showed that >80% of the product was dimer and trimer with 13% tetramer, 5% pentamer, and 1% hexamer (FIG. 2).

Based on both the GC and NMR data, 1-hexene undergoes exclusively 1,2-addition under the reaction conditions. No stereochemical control is exerted by the catalyst which leads to the presence of diasteriomeric alkenes for oligomers with n≥4. These diasteriomers are readily observed in the GC chromatogram (FIG. 2), although sufficient resolution was not obtained to fully separate the two tetramer isomers. The heavier oligomers are not suitable for use as fuels, but hydrogenated versions are expected to have utility as high-performance lubricants. The dimer was separated by fractional distillation at atmospheric pressure, while the trimer was separated by fractional distillation under reduced pressure to give pure samples of each hydrocarbon. Small traces of the next highest oligomer were observed by GC but not by NMR spectroscopy. The pure alkenes were then hydrogenated over Pd/C to yield the saturated compounds. This step is essential to improve the stability of the fuels. In the case of the trimer, hydrogenation yielded a pair of diasteriomers due to the presence of two stereocenters, but the similarity of the chemical shifts between the two molecules resulted in resolution of only 24 peaks in the $^{13}$C NMR (see Supporting Information). For use as fuels, the presence of diasteriomers is important for depressing the freezing point and improving the low temperature viscosity of the hydrocarbons.

After the initial characterization of the pure saturated hydrocarbons, their key fuel properties were determined (Table 1). The density of the dimer fuel is 0.75 g/mL, below the specification for commercial jet fuel and the military jet fuel JP-8 (d>0.775 g/mL). This is common for acyclic paraffins and synthetic paraffinic kerosene (SPK) fuels that make up the bulk of renewable jet fuels. The lower density of the kerosenes compared to conventional jet fuel is due to the lack of aromatics and cycloparaffins in the renewable fuels. The trimer, with a density of 0.78 g/mL does meet the required density for jet fuel, but its relatively high viscosity would preclude its use as a standalone fuel. To address density and viscosity issues, as well as to incorporate aromatics which are essential for maintaining engine integrity, these fuels can be mixed with conventional hydrocarbon fuels. In fact, emerging renewable fuels are commonly tested as 50:50 blends with petroleum based fuels. Another key property of alternative fuels is their flashpoint. Both the dimer and trimer have significantly higher flashpoints than JP-8, or even high flashpoint jet fuel used by the US Navy (JP-5 >60° C.). These high flash points greatly reduce the risk of fire and make these fuels well suited for use in demanding environments.

TABLE 1

Key Fuel Properties of Hexene Oligomer Fuels

| Property | Dimer | Trimer | Dodecane | JP-8 |
| --- | --- | --- | --- | --- |
| Density (g/mL) | 0.75 | 0.78 | 0.75 | 0.80 |
| Flashpoint (° C.) | 74 | 128 | 74 | >38 |
| Viscosity (−10° C.)$^a$ | 3.03 | 17.2 | solid | <8.0$^b$ |
| Viscosity (40° C.)$^a$ | 1.10 | 3.1 | NM | NA |
| Cetane No. | 67 | 92 | 88 | >42 |
| Freezing Point (° C.) | −77 | — | −9 | <−47 |

$^a$units: mPa · s.
$^b$at −20° C.

Figure 3:
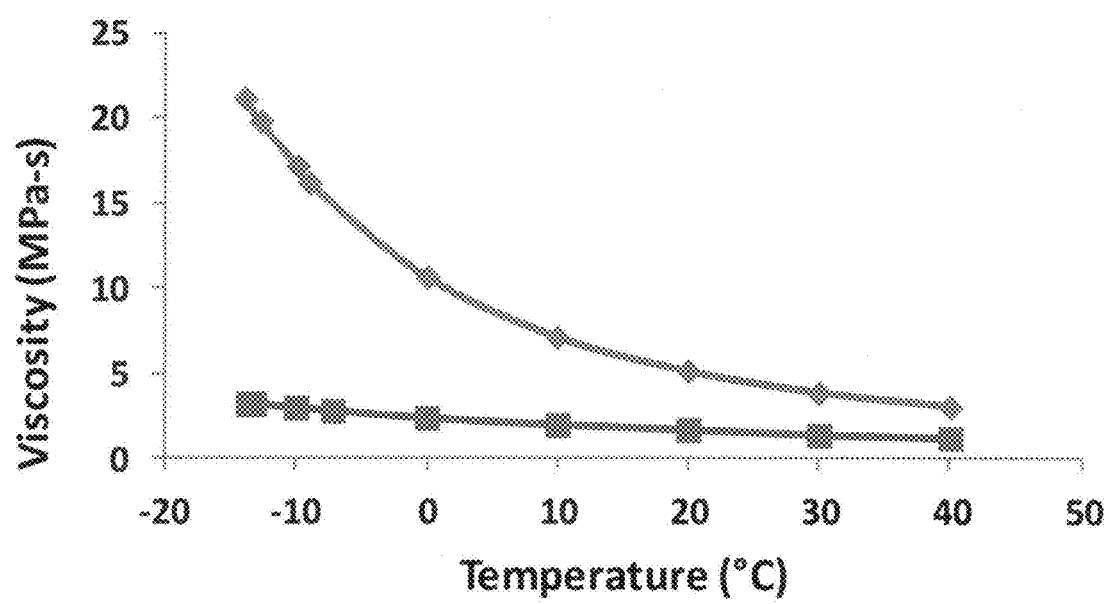
FIG. 3 is a graph illustrating viscosity of the dimer (■) and timer (◇) fuels from 40° C. to −14° C., according to embodiments of the invention.

To further evaluate these hydrocarbons as both diesel and jet fuels, the viscosities of the dimer and timer were measured from 40 to −14° C. (FIG. 3). As expected, the dimer maintained an exceptionally low viscosity over the entire measured range. The 40° C. viscosity was only 1.10 mPa·s, with a linear increase up to 3.27 mPa·s at −14° C. The viscosity specification for diesel #2 requires a 40° C. viscosity of 2.1 mPa·s, while the −20° C. viscosity is well within the specification for JP-8 (<8.0 mPa·s), with an extrapolated value of 3.56 mPa·s. The trimer has a 40° C. viscosity of 3.1 mPa·s, which is in the middle of the range for diesel #2 (2.1-4.1 mPa·s), while the −20° C. viscosity is 24.5 mPa·s and well above the upper limit for jet fuel. Based on this data, it's clear that the dimer has properties commensurate with jet fuel, while the trimer has properties consistent with diesel fuel. Although each fuel has a direct application, it follows that significant amounts of the dimer could be blended with conventional diesel fuel and conversely, significant amounts of the trimer could be blended with petroleum-derived jet fuel.

Figure 4:
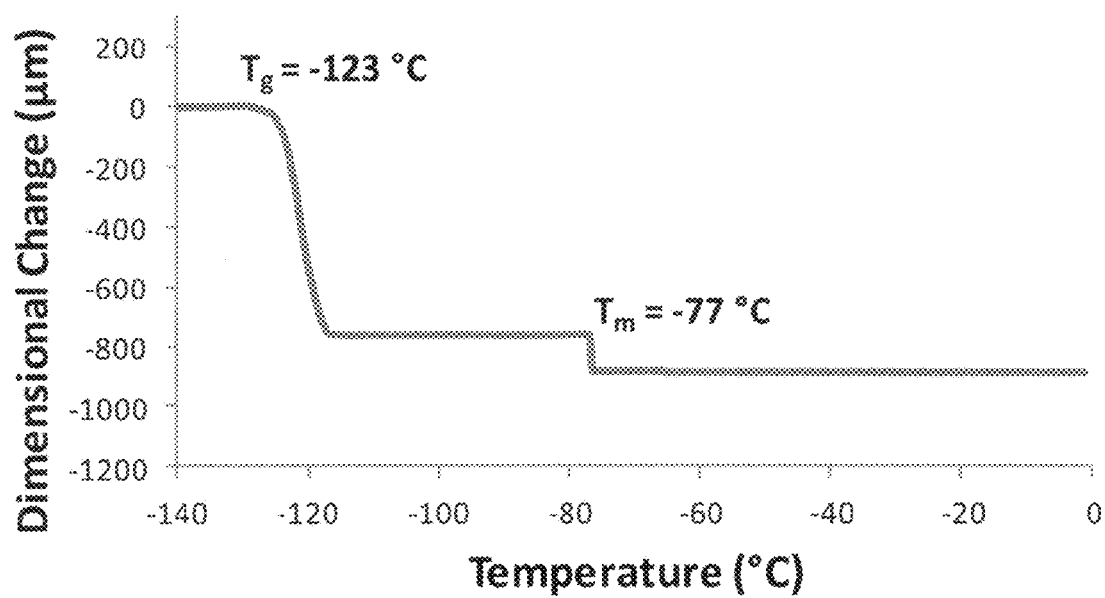
FIG. 4 is a graph illustrating the thermomechanical analysis of the hydrogenated dimer, according to embodiments of the invention.
Figure 5:
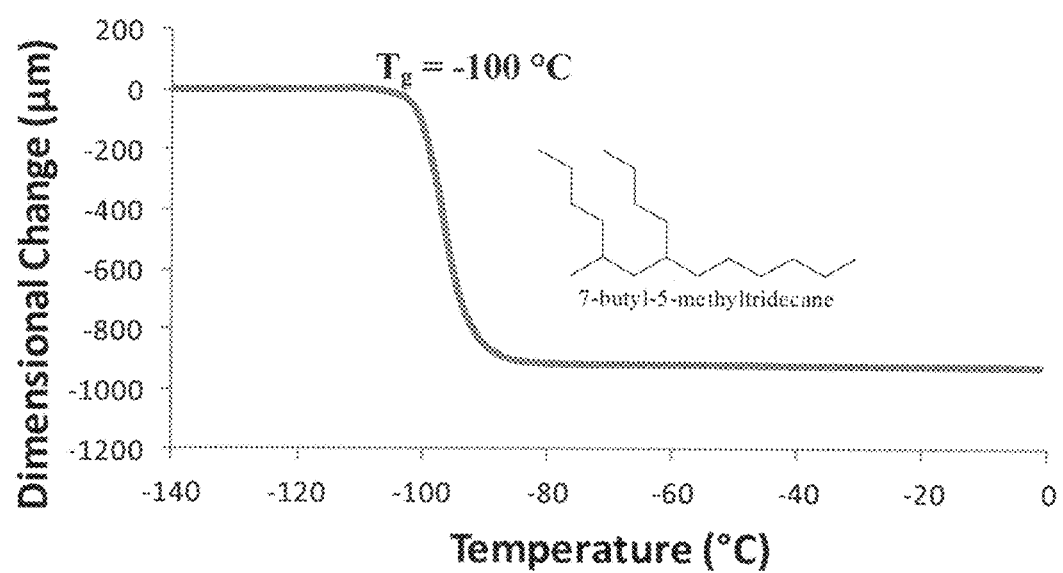
FIG. 5 is a graph illustrating the thermomechanical analysis of the hydrogenated trimer, according to embodiments of the invention.

In addition to viscosity, an acceptable freezing point is critical for jet fuels. Low temperatures at high altitude require freezing points below −47° C. for JP-8. Differential scanning calorimetry (DSC) was initially utilized to determine the freezing point of both the hydrogentated dimer and trimer, however, neither sample showed a significant endotherm during the heating cycle, nor an exotherm during the cooling cycle. Based on recent success in probing tow temperature transitions of fuels with TMA, this technique was applied in the current case. The dimer exhibited a sharp transition at −77° C. corresponding to the freezing point (FIG. 4). The glass transition temperature of this hydrocarbon could also be observed as a slow change in the probe height at −123° C. A freezing point for the trimer could not be determined, but the $T_g$ was observed at −100° C. (FIG. 5). This excellent low temperature performance can be compared to conventional diesel #2 which begins to cloud at −0° C. and gels at ∼−10° C.

A key parameter for diesel fuel is the cetane number. This value is a measure of the relative ability of hydrocarbons to combust under compression ignition conditions. Hydrocarbons with long, straight chains improve the cetane number of fuel, while aromatics and branched chain hydrocarbons greatly decrease the cetane number. In the current case the hydrocarbons are modestly branched, i.e. (one branch site)/(12 carbons) for the dimer and (one branch site)/(9 carbons) for the trimer. Although methyl branches are quite prevalent in conventional fuels, butyl branches are not and k was unclear what effect the modest branching of the trimer would have on the cetane number. In our previous experience with butene oligomer fuels, it was observed that a blend of C12 and C16 molecules with 2 or 3 branches, respectively, had a cetane number of 55. Based on this result, we expected the hexene-derived fuels to have cetane numbers greater than 60. The cetane number for pure solutions of both the dimer and trimer were determined by IQT. The dimer had a cetane number of 67, while the trimer had a remarkable cetane number of 92. These values are less than the linear alkanes of the same molecular weight, with dodecane having a cetane number of 88 and n-octadecane having a cetane number of 103, but quite remarkable compared to diesel #2 which only requires a cetane number of 42. The exceptional cetane numbers of these renewable fuels suggests that they may have utility as blendstocks to improve the cetane number of petroleum-based fuels.

In summary, renewable jet and diesel fuels can be readily generated from 1-hexene by a controlled oligomerization process. Coupling the current work with the near quantitative yields reported in the literature for ethanol dehydration and ethylene trimerization, the overall process for converting bio-ethanol to jet/diesel fuels and biolubricants is >92% carbon efficient. Due to the exquisite control of the products imparted by the metallocene catalyst, the fuels produced by this method can in some cases outperform conventional petroleum-based fuels. The synthesis of renewable hydrocarbons that significantly improve the performance characteristics of petroleum based fuels represents a paradigm shift in the development of alternative fuels.

The outlook for producing these fuels on an industrial scale is promising. Given the existing infrastructure for the production and utilization of both ethylene and 1-hexene, the current process could be readily integrated into existing facilities. The versatility of this approach which can utilize either bio-ethanol or petrochemical ethylene as a feedstock renders this process a dynamic alternative to other bottom-up synthetic jet/diesel production processes including conventional GTL technology and Fischer-Tropsch catalysis.

Example 1: One equivalent of $Cp_2ZrCl_2$ is dissolved in a 10% MAO solution (toluene) to generate a solution with Al:Zr=50. The pale yellow solution is stirred for one h and the solvent removed in vacuo to give a bright yellow solid. Rigorously dry 1-hexene (10,000 equivalents) is added to the flask which is maintained at 5° C. with an ice bath. The mixture is allowed to reach ambient temperature and is maintained at that temperature and vigorously stirred until the 1-hexene is fully consumed. After the reaction is complete, the catalyst is quenched with a stoichiometric amount of water and the hydrocarbon mixture is filtered and transferred to a hydrogenation apparatus. The mixture is hydrogenated with Pd/C under a hydrogen atmosphere (50 psi) to generate a fully saturated fuel. The fuel mixture is then fractionally distilled to isolate a $C_{12}$ cut, a $C_{18}$ cut, and a $C_{24}+$ cut.

Embodiments of the invention generally relate to methods for converting ethanol to turbine and/or diesel fuels including, dehydrating ethanol by the use of at least one heterogeneous catalyst to produce ethylene, converting the ethylene into 1-hexene by reacting the ethylene with a selective or unselective oligomerization catalyst to produce pure 1-hexene or a mixture including 1-hexene, converting the 1-hexene into a mixture of dimer(s) and trimer(s) by reacting the 1-hexene with a Ziegler Natta catalyst, and hydrogenating with a hydrogenation catalyst and distilling the mixture of dimer(s) and trimer(s) to produce a $C_{12}$ turbine/jet fuel, $C_{18}$ diesel fuel, and residues.

In embodiments, the ethanol is dehydrated to the ethylene in a continuous process utilizing a low acidity alumina catalyst at elevated temperature ranging from about 250° C. to about 400° C. and under an inert atmosphere. In embodiments, the ethylene is thoroughly dried by passage through a suitable drying agent. In other embodiments, the ethylene is condensed under increased pressure or utilized in a multi-step, downstream process. In embodiments, the unselective catalyst(s) and a fractional distillation is used to isolate pure 1-hexene. Embodiments further include separating into a $C_6$-$C_8$ fraction, a $C_{10}$-$C_{14}$ fraction, a $C_{16}$-$C_{20}$ fraction, and a $C_{20+}$ fraction when the unselective oligomerization catalyst(s) is used. In embodiments, the $C_6$-$C_8$ fraction is selectively oligomerized with a Ziegler-Natta catalyst, the $C_{10}$-$C_{14}$ fraction is directly hydrogenating and incorporating into the jet/diesel fuel formulation, and the $C_{16}$-$C_{20}$ fraction is incorporating in limited amounts up to about 20% in jet fuels or significant amounts in diesel fuel.

In embodiments, the Ziegler-Natta catalyst(s) are metallocene based catalysts of the group 4 elements selected from the group consisting of Ti, Zr, Hf, other like catalysts, and any combination thereof. Embodiments further include adding at least one cocatalyst including aluminum alkyls or methylaluminoxane. In embodiments, the 1-hexene is pure 1-hexene or a mixture of 1-hexene/1-octene and is oligomerized to produce a product mixture primarily of the dimers and trimers. In embodiments, when using the pure 1-hexene, the products are 5-methyleneundecane and/or 7-butyl-5-methyleneundecane. In embodiments, the cocatalyst(s) is added to achieve M:Al ratios of from about 1 up to about 500 and said Ziegler Nana catalyst(s) is added in olefin: M ratios of from about 10,000,000:1 to about 5000:1.

In embodiments, the ethylene is generated from a renewable source and/or a petrochemical source. In other embodiments, the ethanol is from a renewable source selected from the group consisting of sugars, cellulosic or lignocellulosic feedstocks, $CO_2$, and bio-derived syngas. In embodiments, the heterogeneous catalyst(s) includes alumina. In embodiments, the oligomerization catalyst includes an ethylene trimerization catalyst that is Ti, Cr, Ta, or Zr-based. In other embodiments, the catalyst includes a highly selective chromium and titanium based catalyst(s) utilized to produce exclusively 1-hexene. In embodiments, the second Ziegler Natta catalyst is either a batch or continuous process.

Embodiments further include adding at least one chain transfer catalyst. In other embodiments, the chain transfer agent is a zinc alkyl compound added to alter the distribution of the dimer(s) and trimer(s) (oligomers). In embodiments, the zinc alkyl loading for an olefin is M ratio of 100:1 is between 2 and 8 equivalents. Embodiments, further include catalytically hydrogenating the dimer(s) and trimer(s)(oligomers) with catalysts selected from the group consisting of nickel, palladium, platinum, and ruthenium catalysts under a hydrogen atmosphere. In embodiments, the hydrogenation includes temperatures ranging from ambient up to 200° C. and at pressures from 1 atm up to about 50 atm. In embodiments, the residue is further vacuum distilled to produce synthetic oil. Another aspect of the invention relates to turbine and diesel Fuels produced by the methods described herein.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for converting ethanol to turbine and/or diesel fuels, comprising:
   dehydrating ethanol by the use of at least one heterogeneous catalyst to produce ethylene;
   converting said ethylene into 1-hexene by reacting said ethylene with a selective oligomerization catalyst that produces exclusively 1-hexene as the primary product, or an unselective oligomerization catalyst that generates a mixture of alpha olefins including 1-hexene;
   converting said 1-hexene into a mixture of dimer(s) and trimer(s) by reacting said 1-hexene with a Ziegler Natta catalyst and a cocatalyst at a temperature ranging from ambient to about 60° C.; and
   hydrogenating said mixture of dimer(s) including 5-methylundecane and trimer(s) including 7-butyl-5-methylundecane with a hydrogenation catalyst to form a mixture of hydrogenated dimer(s) including 5-methylundecane and trimer(s) including 7-butyl-5-methyltridecane and distilling said mixture of hydrogenated dimer(s) and trimer(s) to produce a $C_{12}$ turbine/jet fuel with a density of about 0.75 g/mL, a flashpoint of about 74 C, and a cetane number of about 67; a $C_{18}$ diesel fuel with a density of about 0.78 g/mL, a flashpoint of about 128° C., and a cetane number of about 92; and residues.

2. The method according to claim 1, wherein said ethanol is dehydrated to said ethylene in a continuous process utilizing a low acidity alumina catalyst at elevated temperature ranging from about 250° C. to about 400° C. and under an inert atmosphere.

3. The method according to claim 1, wherein said ethylene is dried by passage through a drying agent.

4. The method according to claim 1, wherein said ethylene is condensed under increased pressure or prepared in a continuous process.

5. The method according to claim 1, wherein said oligomerization catalyst and a fractional distillation is used to isolate 1-hexene.

6. The method according to claim 1, wherein said conversion of ethylene produces a $C_{6+}$+ olefin fraction in addition to said 1-hexene and further comprising separating the $C_{6+}$ olefin fraction into a $C_6$-$C_8$ fraction, a $C_{10}$-$C_{14}$ fraction, a $C_{16}$-$C_{20}$ fraction, and a $C_{20}$+ fraction.

7. The method according to claim 6, wherein said $C_6$-$C_8$ fraction is selectively oligomerized with a Ziegler-Natta catalyst to generate a mixture of dimers and trimers, and said $C_{10}$-$C_{14}$ fraction is blended with said $C_{12}$ turbine/jet fuel.

8. The method according to claim 1, wherein said Ziegler-Natta catalyst are metallocene based catalysts of the group 4 elements selected from the group consisting of Ti, Zr, Hf, and any combination thereof.

9. The method according to claim 8, further comprising adding at least one cocatalyst including aluminum alkyls or methylaluminoxane.

10. The method according to claim 1, wherein a mixture of 1-hexene/1-octene is oligomerized to produce a product mixture substantially of said dimer(s) and trimer(s).

11. The method according to claim 10, wherein said oligomerization of 1-hexene produces greater than 81% products 5-methyleneundecane and/or 7-butyl-5-methyleneundecane.

12. The method according to claim 9, wherein said cocatalyst(s) is added to achieve metal/aluminum ratios of from about 1 up to about 500 and said Ziegler Natta catalyst is added in olefin:catalyst ratios of from about 10,000,000:1 to about 5000:1.

13. The method according to claim 1, wherein said ethylene is generated from a renewable source and/or a petrochemical source.

14. The method according to claim 1, wherein said ethanol is from a renewable source selected from the group consisting of sugars, cellulosic or lignocellulosic feedstocks, $CO_2$, and bio-derived syngas.

15. The method according to claim 1, wherein said heterogeneous catalyst(s) includes alumina.

16. The method according to claim 1, wherein said oligomerization catalyst includes an ethylene trimerization catalyst that is Ti, Cr, Ta, or Zr-based.

17. The method according to claim 1, wherein said selective oligomerization catalyst is a chromium or titanium based catalyst and is selective towards 1-hexene formation.

18. The method according to claim 1, wherein said oligomerization conversion of 1-hexene is conducted with a Ziegler-Natta catalyst is either a batch or continuous process.

19. The method according to claim 1, further comprising adding at least one chain transfer catalyst to said Ziegler Natta catalyst.

20. The method according to claim 19, wherein said chain transfer catalyst is a zinc alkyl compound added to alter the distribution of said dimer(s), trimer(s), and heavier oligomers.

21. The method according to claim 20, wherein said zinc alkyl compound to Ziegler Natta catalyst (M) ratio is from about 2 to 8 when the Al:Ziegler Natta catalyst (M) ratio is 100:1.

22. The method according to claim 1, further comprising catalytically hydrogenating said dimer(s), trimer(s), and heavier oligomers with catalysts selected from the group consisting of nickel, palladium, platinum, and ruthenium catalysts under a hydrogen atmosphere.

23. The method according to claim 1, wherein said hydrogenation includes temperatures ranging from ambient temperature up to 200° C. and pressures from 1 atm up to about 50 atm.

24. The method according to claim 1, wherein said residues are further vacuum distilled to produce synthetic oil.

25. The method according to claim 6, wherein said $C_{10}$-$C_{14}$ fraction and/or $C_{16}$-$C_{20}$ fraction is blended with said $C_{18}$ diesel fuel.

* * * * *